US012239835B2

(12) United States Patent
Serov

(10) Patent No.: US 12,239,835 B2
(45) Date of Patent: Mar. 4, 2025

(54) METHOD FOR PROTECTING BIOLOGICAL OBJECTS FROM THE NEGATIVE INFLUENCE OF TECHNOGENIC ELECTROMAGNETIC RADIATION

(71) Applicant: UAB "TECHNANO", Vilnius (LT)

(72) Inventor: Igor Serov, Girona (ES)

(73) Assignee: Dimitry Serov, Richmond Hill (CA)

( * ) Notice: Subject to any disclaimer, the term of this patent is extended or adjusted under 35 U.S.C. 154(b) by 439 days.

(21) Appl. No.: 17/765,734

(22) PCT Filed: Oct. 1, 2019

(86) PCT No.: PCT/IB2019/058334
§ 371 (c)(1),
(2) Date: Mar. 31, 2022

(87) PCT Pub. No.: WO2021/064446
PCT Pub. Date: Apr. 8, 2021

(65) Prior Publication Data
US 2022/0401724 A1 Dec. 22, 2022

(51) Int. Cl.
*A61N 1/16* (2006.01)
(52) U.S. Cl.
CPC .................... *A61N 1/16* (2013.01)
(58) Field of Classification Search
CPC ........................................... A61N 1/16
USPC ........................... 250/515.1, 440.11
See application file for complete search history.

(56) References Cited

U.S. PATENT DOCUMENTS 6,709,745 B2  3/2004  Kuehnert
2011/0065975 A1*  3/2011  Kazanskiy ............... A61N 2/02
                                                 29/846

FOREIGN PATENT DOCUMENTS

RU      2265898 C2    12/2005
WO   1997034459 A2     9/1997

OTHER PUBLICATIONS

International Search Report and Written Opinion mailed Jun. 22, 2022 for PCT Application No. PCT/IB2020/058334.

* cited by examiner

*Primary Examiner* — Jason L McCormack
(74) *Attorney, Agent, or Firm* — Koivula & Somersalo, LLC

(57) ABSTRACT

The method for protecting biological objects (BO) from the negative influence of technogenic electromagnetic (EM) radiation in a wide range of frequencies, which consists of creating a coherent field in the form of a fractal matrix around a biological object using a fractal-matrix as coherent transducer based on a self-affine annular raster lattice (resonator) formed from ringed topological lines, which create a slit-like raster, and is a universal Fourier transformer that harmonizes the amplitude, phase, frequency and polarization vector of external technogenic radiation and the BO's own EM radiation. The transformation of external radiation occurs in accordance with the Fourier transform with the formation of a coherent matrix of EM wave superpositions. The coherent matrix does not conflict with the BO. The transformation does not affect the functioning of the technical devices. The coherent transformer can be placed on the BO, or between the BO and the source.

7 Claims, 15 Drawing Sheets

Result of performing affine transformations

Wafer orientation relative to the coordinate system (a) on surface (b) at 0.1 mm (c) at 0.2 mm (d) at 0.3 mm (e) at 0.4 mm (f) at 0.5 mm (g) at 0.6 mm (h) at 0.7 mm (j) at 0.8 mm (k) at 0.9 mm (l) at 1.0 mm (m) at 1.1 mm (n) at 1.2 mm (o) at 1.3 mm (p) at 1.4 mm (r) at 1.5 mm (s) at 1.6 mm (t) at 1.7 mm

METHOD FOR PROTECTING BIOLOGICAL OBJECTS FROM THE NEGATIVE INFLUENCE OF TECHNOGENIC ELECTROMAGNETIC RADIATION

FIELD OF INVENTION

The invention relates to methods for protecting biological objects from the negative influence of technogenic electromagnetic radiation in a wide range of frequencies. The invention relates to protective technologies, industrial and sanitary hygiene, and occupational safety.

BACKGROUND ART

The invention relates to methods for protecting biological objects (BO) from technogenic electromagnetic (EM) radiation in a wide range of frequencies and can be used in the everyday life of each person to protect against the negative influence of surrounding technogenic radiation, including 5G mobile communication systems (3.5-28 GHz).

Known methods for protecting, blocking, scattering and absorbing a signal: RU2194376, RU2265898, RU2234175.

Patent RU2194376/WO1997034459 relates to a method of transferring a layer onto a detail which shields against electromagnetic radiation. The layer is transferred with a predetermined extension directly or indirectly on to the detail with the help of a known printing method.

Patent RU2265898 relates to protection from electromagnetic emission. It describes mesh of electric-conductive material which is positioned on dielectric transparent film with applied transparent electric-conductive layer, made either of indium, or of tin, or of indium/tin alloy with thickness, approximately equal to 0.1 of skin layer, and the very mesh is applied with thickness not exceeding skin-layer by printer or plotter using electric-conductive compound, consisting of ultra-dispersive electric-conductive powder with stable electric conductivity and average size of particles 10.0-600.0 nm, polymer linking component, organic solvent and surfactant with certain ratio of components. The obtained effect is forming of transparent screens, screening properties of which do not depend on falling angle of electromagnetic emission, also light and simple to manufacture.

Patent DE10039125A1/RU2234175 discloses electromagnetic absorber granulate consisting of a highly porous glass and/or ceramic granulate coated or filled with ferrite and/or an electrically conducting material. An independent claim is also included for a process for the production of a coated absorber granulate comprising finely grinding the ferrite and/or electrically conducting material, and applying with a binder as suspension to the glass and/or ceramic granulate. Preferred Features: The electrically conducting material is a metal and/or carbon. The granulate grain size is 0.2-5 mm and the coating has a thickness of 10-300 mu m. The ferrite is made of an Mn—Zn, Ni—Zn, Ba, Sr ferrite or a Sc-, Co-, or Ti-substituted hexaferrite with a garnet structure.

The shortcoming of these methods is the loss of the signal, its distortion, a change of the natural background, inconvenience, and complexity of use.

Before proceeding to the description of the invention, it should be noted that all methods for protecting a biological object from technogenic EM radiation come down to reducing the intensity of the EM pulse, reducing the exposure time, or increasing the distance from the biological object to the radiation source, which leads to inconvenience or the inability to properly use the source of EM radiation, especially when using it to transmit large amounts of information.

SUMMARY OF INVENTION

The task for which the claimed invention is intended is to protect a biological object, in particular the human body, from the negative influence of technogenic EM radiation of a wide range of frequencies without reducing the effectiveness of the sources generating it and without imposing additional requirements on them.

In this aspect, it is most rational to change the structure of the EM pulse arising from the radiation source, transforming it into a form safe for the BO, without losing its effectiveness.

The restructuring of technogenic EM radiation in the proposed method implies changing its amplitude-frequency spectrum from an arbitrary form to a coherent form through the influence of a coherent field created by a transformer that initiates the process of counter-harmonization of amplitudes, phases, frequencies, polarization vectors, and the EM radiation incident on it.

This process, which is implemented by using a coherent transformer (resonator), is proven and protected (Russian Federation Patent No. 2231137, No. 2217181, No. 2284062) and is later described in more detail.

The coherent transformer can be placed on the biological object BO, next to it, on the source of technogenic radiation, or between the BO and the source (FIG. 1).

DESCRIPTION OF DRAWINGS

In order to understand the invention better and appreciate its practical applications, the following pictures are provided and referenced. Figures are given as examples only and in no way shall limit the scope of the invention.

FIG. 7a— amplitude; FIG. 7b— phase.

FIG. 8a— amplitude; FIG. 8b— phase.

FIG. 10a— amplitude; FIG. 10b— phase.

DETAILED DESCRIPTION OF PREFERRED EMBODIMENTS

The claimed method is based on self-affine holographic objects' ability to transform the EM pulses interacting with them according to their characteristics.

Holography (from ancient Greek: ὅλος—whole, γράφω—I writing) is based on two physical phenomena-diffraction and interference of EM waves. The physical idea is that under the imposition of several wave pulses, under certain conditions, an interference pattern occurs, that is, a spatial regular system of maxima and minima of the intensity of electromagnetic radiation in the form of a stationary field having a fractal self-affine structure.

According to contemporary scientific concepts, when interacting with external EM radiation, any regular structure creates a periodic EM field (superposition).

In order for this interference pattern to be stable for the time necessary to observe, and in order for it to be recorded, these EM pulses must be harmonized spatially and temporally across frequencies and amplitudes. Such EM waves are called coherent.

Based on the principle of superposition, if EM waves coincide in phase, then they add with each other and produce a resultant wave with an amplitude equal to the sum of their amplitudes. If they meet in antiphase, then they cancel each other out. If two opposite EM pulses are identical in phase, amplitude, frequency, and polarization vectors, then their amplitudes are multiplied.

The resulting interaction of two coherent waves is a fractal standing wave. That is, the interference pattern will be stable in time (phase), in amplitude (power), polarization vector (direction), and frequency (stability). Since any fractal construct is a self-affine structure, that is, formed from its own analogues, this property underlies the production and restoration of holograms in its individual fragments.

To obtain a holographic response, the resonator must either itself have the ability to transform the radiation incident on it into a coherent form, or the incident radiation must initially be coherent. The hologram arising from the resonator carries not only the same characteristics and properties as the radiation incident on the resonator, but also the specific features of the resonator topology itself. As a result, if the resonator initiates a coherent transformation of incoherent EM radiation incident on it, the resulting hologram has the same ability to transform an EM pulse of the corresponding frequency range that interacts with it into a coherent state.

The strength and intensity of the coherent field fall in proportion to the square of the distance from the resonator. Thus, the given EM field can transform EM radiation interacting with it into a coherent form, if its strength and intensity is not lower than the strength and intensity of the opposite radiation. Such interaction is possible due to the fractality of the resonator, not only when the frequencies coincide, but also when they are similar at multiple scales.

Figure 1:
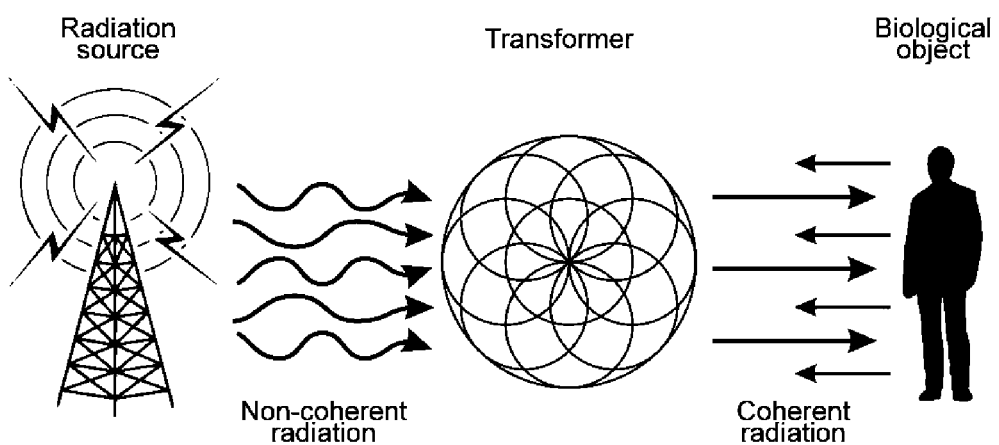
FIG. 1 depicts that the coherent transformer placed on the biological object next to it, on the source of technogenic radiation, or between the biological object and the source.
Figure 2:
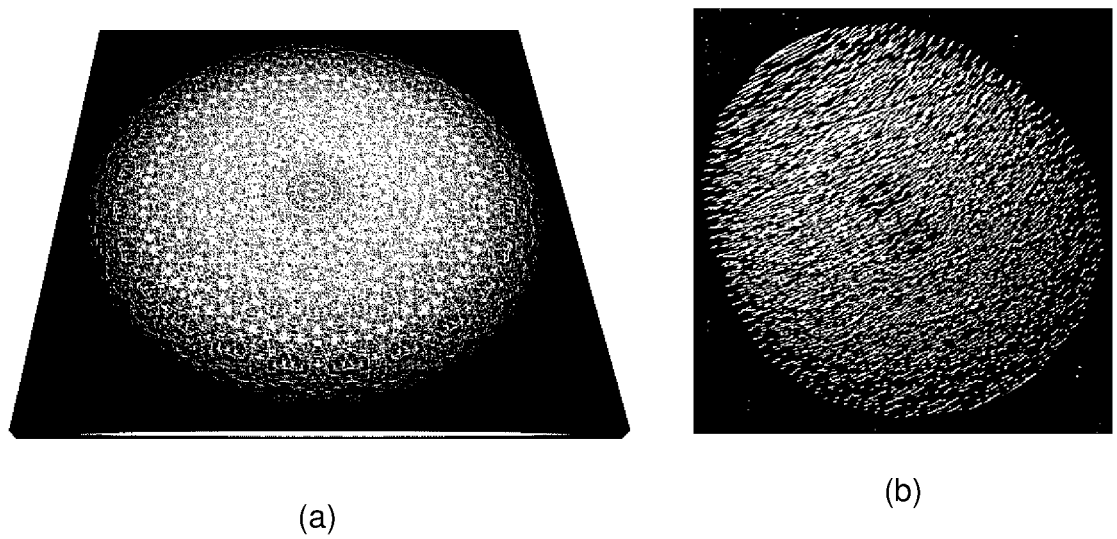
FIG. 2 presents an image of a self-affine lattice fixed on a solid medium (FIG. 2a), and a photograph of the holographic response resulting from the incoherent EM radiation's interaction with the slit topological surface of the lattice (FIG. 2b).

FIG. 2 presents an image of a self-affine lattice fixed on a solid medium (FIG. 2a), and a photograph of the holographic response resulting from the incoherent EM radiation's interaction with the slit topological surface of the lattice (FIG. 2b).

It is known that coherence (cohaerens—in communication) is the harmonized flow in time and in space of several oscillatory processes.

The term "coherence" means the absence of conflicts, consistency, and communication. When applied to EM radiation, it refers to consistency and communication between EM oscillations and waves. Because radiation is distributed across time and space, it is possible to estimate the coherence of oscillations radiated by a source at various points in time at any particular point in space, as well as the coherence of oscillations radiated at a particular point in time at various points in space [8]. Oscillations are called fully coherent if the difference of their phases at the observation point remains constant in time and, when these oscillations are added, determines the amplitude and intensity of the summed (resulting) oscillation. Oscillations (waves) are called partially coherent if the difference of their phases changes very slowly (compared with the observation time), and incoherent if the phase difference changes randomly.

Thus, "coherence" means consistency and communication between EM oscillations. EM radiation is distributed across time and space, so it is possible to estimate the coherence of oscillations radiated by a source at various points in time at any particular point in space (temporal coherence) or the coherence of oscillations radiated at a particular point in time at various points in space (spatial coherence). These properties lead to the conclusion that energy losses at a point of coherent radiation are minimized.

Figure 3:
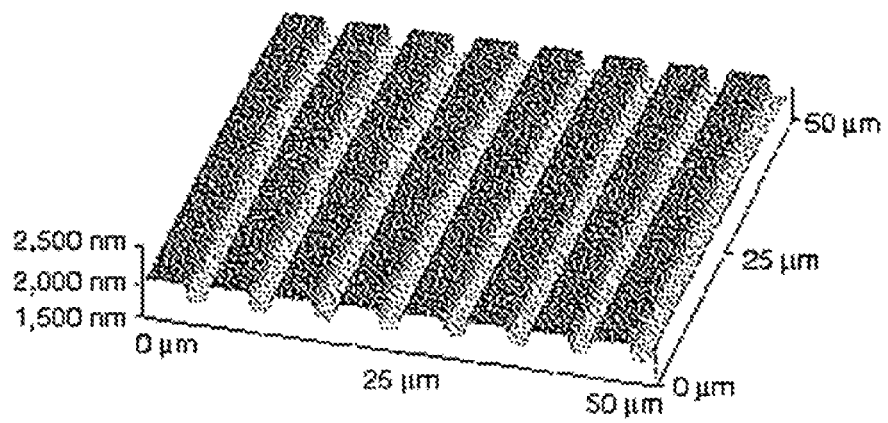
FIG. 3 depicts a wafer of silicon carbide (SiC), which is a source of coherent, nearly monochrome radiation at a distance of 100 nm from the surface of the wafer.

An example of obtaining coherent radiation using a novel approach is creating regular structures on the surface of solids. These structures then act as resonators. An example of this approach [9] is the use of a SiC wafer with a regular structure in the form of parallel grooves, which initiates the production of coherent radiation with a peak at the corresponding wavelength (FIG. 3).

Of interest is the case where it would be possible to generate EM oscillations on not a single frequency, but a wide range of frequencies, while preserving interrelationships between them such that they remain coherent, not only in time, but also in space, like a laser. To do this, we need to use, as a foundation, a certain resonator on a planar substrate, similar to the given example, but with a topographical surface in the form of fractally arranged circles with specific interrelationships.

A device that generates coherent radiation with such properties would find application in a diversity of fields, including for spatial encoding of data, because it can transform incident radiation into a coherent form with properties containing information about the incident radiation.

So-called self-affine structures generated in the form of annular slits open unexpected possibilities for use in scientific research and technology. In [1] a self-affine fractal is defined as a structure that is invariant after simultaneous yet quantitatively different changes in the scale along different spatial axes. The affine transformation of a vector from the origin to point $(x_1, y_1)$, to a vector from point $(b_1, b_2)$ to point $(x_2, y_2)$ is defined as:

$$x_2 = a_{11}x_1 + a_{12}y_1 + b_1$$

$$y_2 = a_{21}x_1 + a_{22}y_1 + b_2$$

Figure 4:
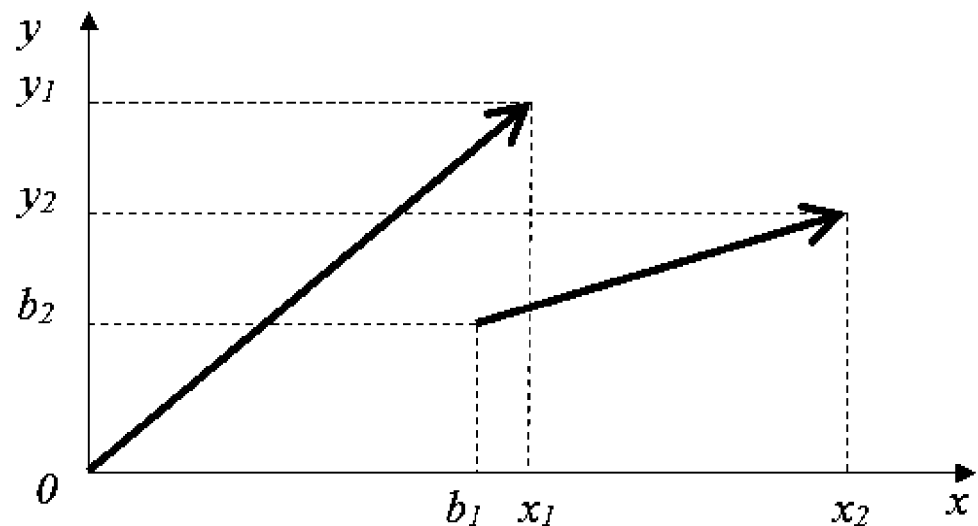
FIG. 4 depicts affine transformations of a vector.

System (1) can be represented as a matrix:

$$T = \begin{bmatrix} a_{11} a_{12} b_1 \\ a_{21} a_{22} b_2 \end{bmatrix}$$

and illustrated in FIG. 4.

Affine transformations can also define a rotation by angle a about the origin.

Figure 5:
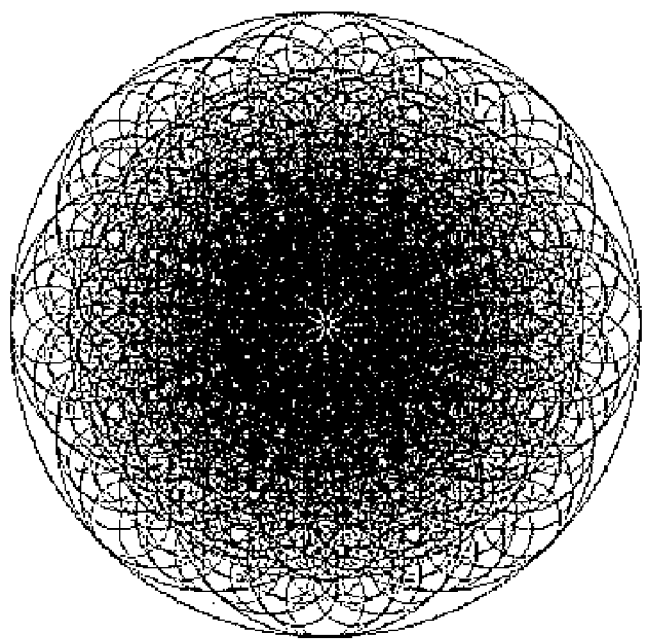
FIG. 5 is the result of performing affine transformations.

After performing transformations representing the multiplication of points of the figure by the scale factor $m_1 = 2^i$ and rotations by an angle proportional to the coefficient $m_2 = 2^i$, and overlaying the original drawing, we obtain the figure shown in FIG. 5.

Figure 6:
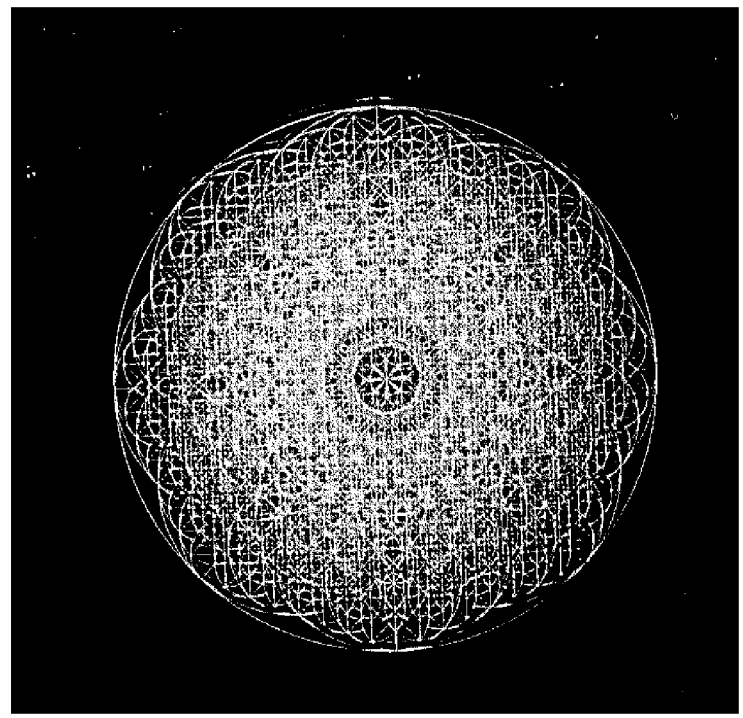
FIG. 6 depicts appearance of a self-affine structure.

The appearance of such a structure is presented in FIG. 6.

Modeling. During the modeling, a stationary model and two-dimensional and three-dimensional non-stationary models were analyzed.

Stationary model. For the stationary case, the interaction of EM radiation waves with the wafer's surface can be written as follows:

$$\frac{\partial^2 E}{\partial \varphi^2} + \frac{\partial^2 E}{\partial r^2} = \left(k^2 - \varepsilon\left(\frac{\omega}{c}\right)^2\right)E$$

where k is the wave number, ε is the wafer's dielectric constant, ω is the cyclic frequency, c is the speed of light; r is the length of the radius vector, φ is the polar angle, E is the electric component of the strength vector.

The following type of model was used during modeling:

$$\frac{\partial^2 E}{\partial \varphi^2} + \frac{\partial^2 E}{\partial r^2} = -a^2 E - b$$

where E is a function proportional to the strength of the radiation; r is the length of the radius vector, φ is a polar angle, a and b are constants.

During calculations on a computer, the radiation's periodic behavior was changed relative to the size of the wafer, when the wavelength of the incident radiation and the periodic behavior of the resonator's surface pattern were compared, taking into account its dimensions.

Figure 7:
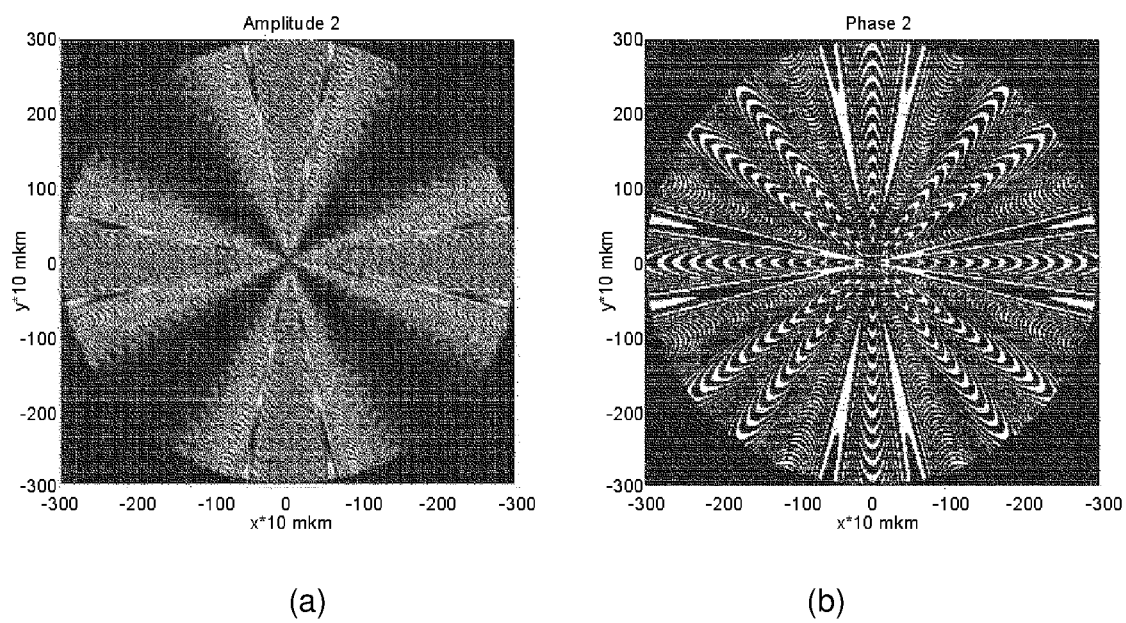
FIG. 7 modeling result for incident radiation with a frequency of 2 periods per 1 rotation by the angle φ.
Figure 8:
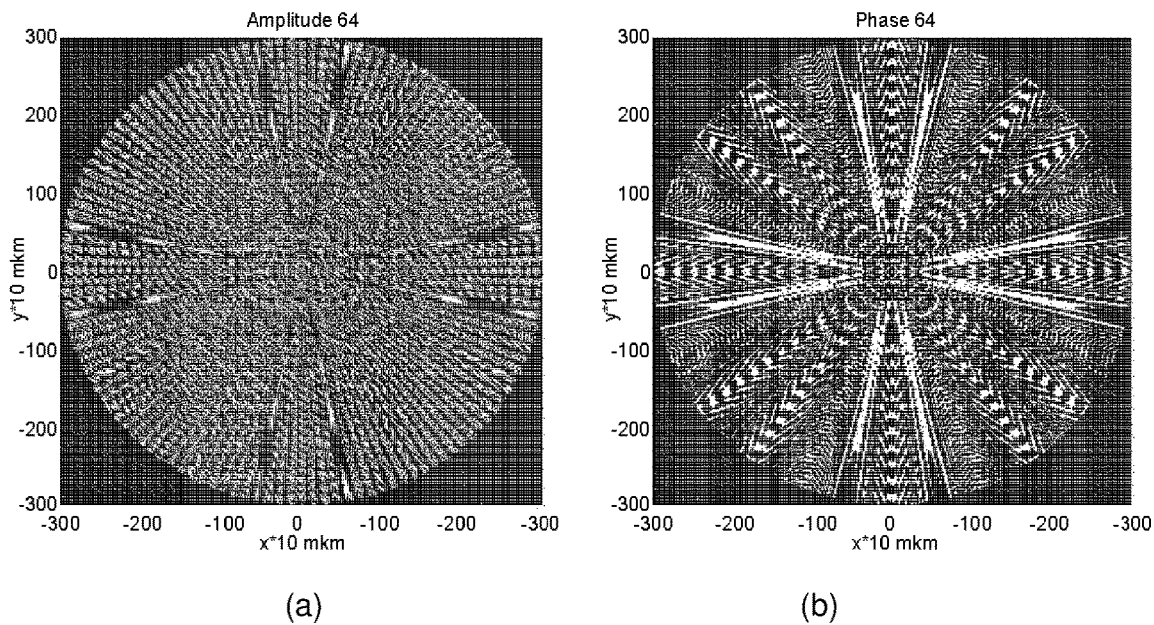
FIG. 8 is presented periodic behavior of incident radiation of 64 periods per 1 rotation by angle φ.

The obtained modeling results, shown in the figures FIG. 7 and FIG. 8, show that the strength of the electric field, after interacting with the self-affine fractal lattice, is redistributed so that the graphs of the field distribution over the surface become regular, a trait that remains almost unchanged when changing the frequency of the incident radiation over a wide range.

Non-stationary model. The fractal served as the foundation for building the mathematical model.

The rings on the surface are grooves about 1.3 microns deep and 1 μm wide. The minimum distance between the "grooves" is 1 μm. The wafer's outer diameter was 6 mm. When interacting with the conductor, an electric field causes charges to shift and increases the concentration of charges in the "grooves" relative to adjacent areas.

Therefore, during modeling, it was assumed that the medium's charges would be concentrated more in the "grooves" than in other areas. When the potential reaches some critical value, there is a discharge along the shortest distance between the grooves.

Non-stationary two-dimensional model. In this case, the mathematical model looks like this:

$$\frac{\partial E}{\partial t} = D\left(\frac{\partial^2 E}{\partial x^2} + \frac{\partial^2 E}{\partial y^2}\right) - aE$$

where D and a are coefficients, E is the electric field's strength, x and y are coordinates, and t is time. The discharge criteria is implemented as follows: if $|E| > E_{\kappa p}$, then E=0.

The main result of the modeling is that regardless of the conditions at the boundary, the steady-state solution is stable and soliton-like. Its shape does not change with changing boundary conditions. This means that the resonator's self-affine surface transforms radiation in such a way that the result of this process does not depend on the characteristics of the radiation incident on it.

Figure 9:
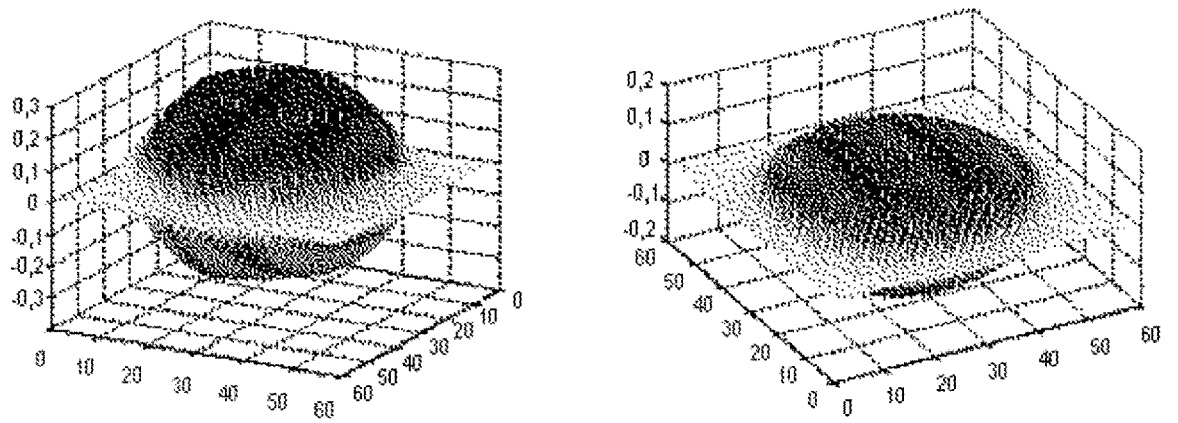
FIG. 9 is presented distribution of strength E across the wafer's surface under the steady state; various projections.
Figure 9:
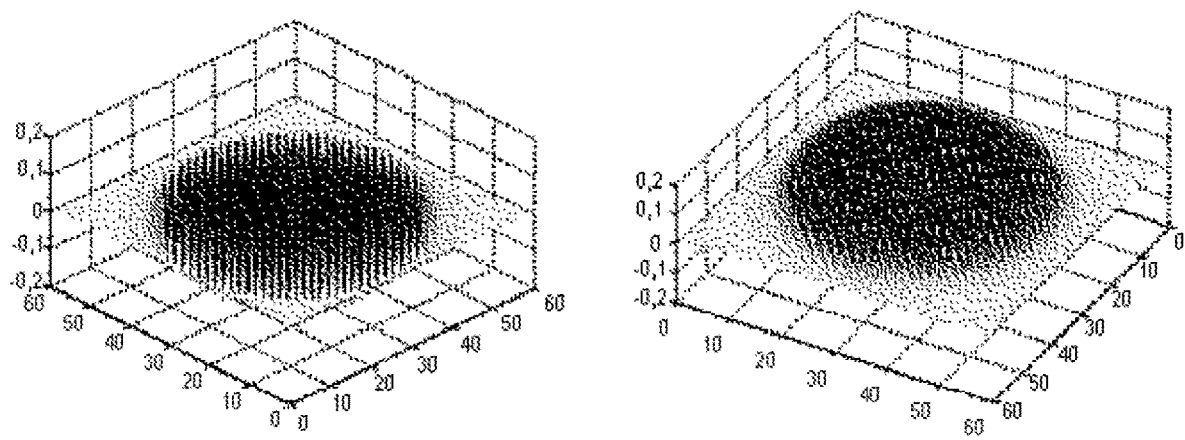
Figure 10:
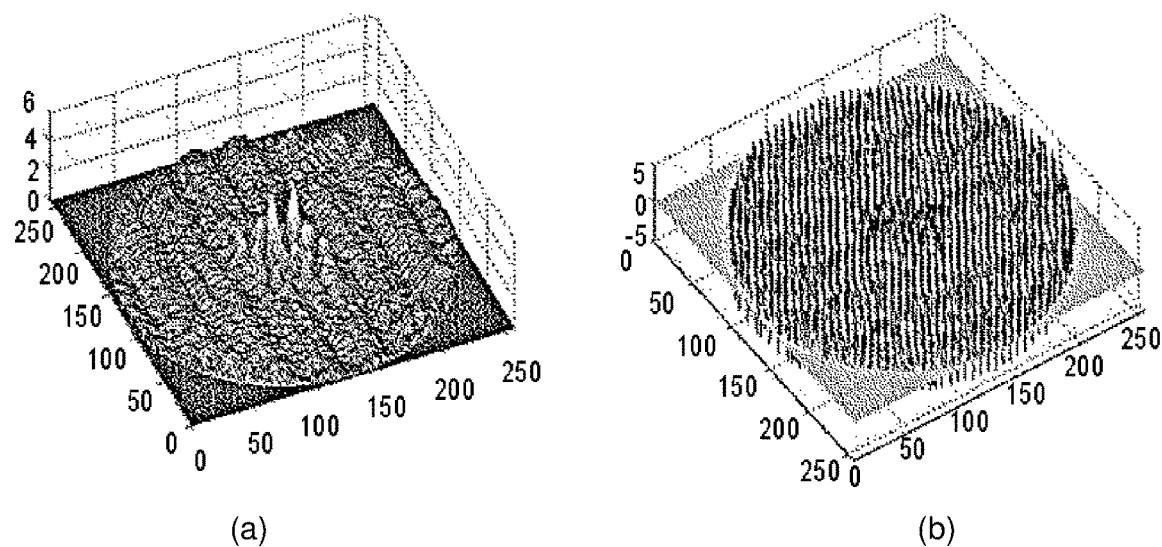
FIG. 10 is presented distribution of the amplitude's spectral power density on the wafer's surface through time $t > t_{test}$.

The results of the calculations for the two-dimensional model (5) are given in the figures FIG. 9 and FIG. 10. FIG. 9 shows distribution of strength E across the wafer's surface under the steady state; various projections. FIG. 10 shows distribution of the amplitude's spectral power density on the wafer's surface through time t>test. Amplitude is presented in FIG. 10a, phase-in FIG. 10b.

Figure 11:
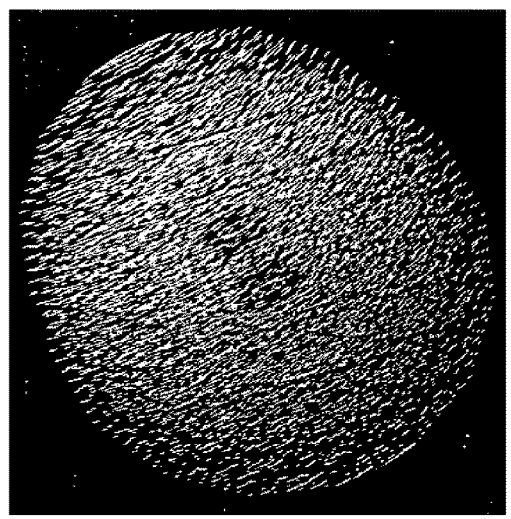
FIG. 11 is presented result of the experiment while illuminating the surface of the resonator's wafer by a halogen lamp.

For comparison, the result of the experiment while illuminating the wafer's surface (illuminating the surface of the resonator's wafer by a halogen lamp) is presented in FIG. 11. The figure clearly shows a luminous "scaly" dome (hologram), similar to the results of a computational experiment.

Non-stationary three-dimensional model. A three-dimensional model was considered:

$$\frac{\partial E}{\partial t} = D\left(\frac{\partial^2 E}{\partial x^2} + \frac{\partial^2 E}{\partial y^2} + \frac{\partial^2 E}{\partial z^2}\right) - aE$$

Figure 12:
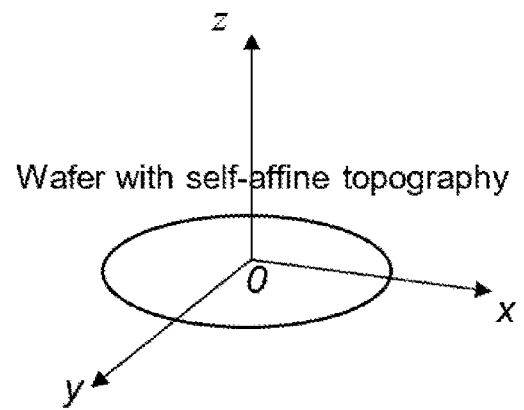
FIG. 12 is presented the resonator's surface lying in plane x0y with the origin at the center of the resonator. The z-axis is orthogonal to this plane.

Technically, this model only differs from the two-dimensional model by the presence of a third spatial coordinate z. However, this makes it possible to create a more complete representation of the interaction of the self-affine topological surface with radiation, and obtain the spatial distribution of strength E. The resonator's surface lies in plane x0y with the origin at the center of the resonator and the z-axis is orthogonal to this plane (FIG. 12).

Figure 13:
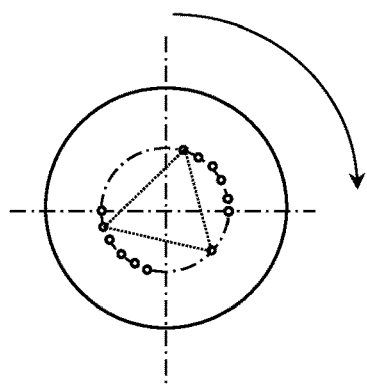
FIG. 13 presents influence on 3 points with an ungrounded center.

Impulse effect on three opposite points with an ungrounded resonator center. Result of modeling with an impulse effect on three points positioned at an angle of 120° from each other (FIG. 13).

Figure 14:
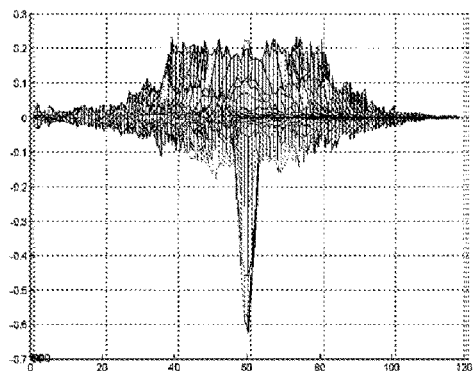
FIG. 14 is presented electric field strength above the resonator. Development of a spatial wave from the surface of the resonator (lower graph), side view.
Figure 14:
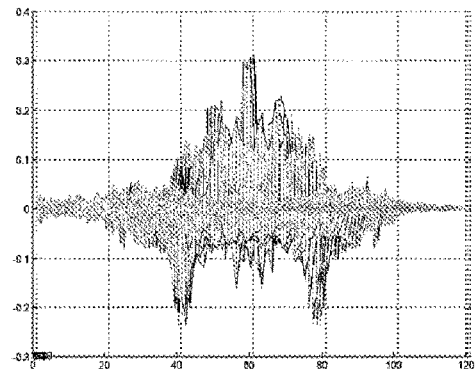
Figure 14:
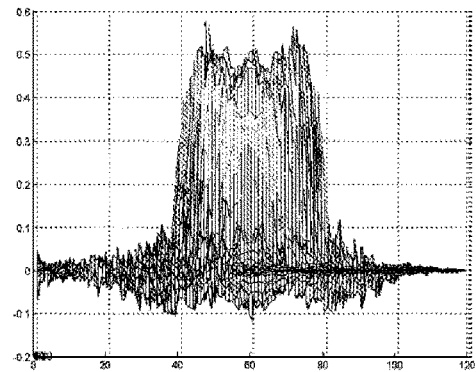

The graphs of the distribution of the electric field strength above the resonator in the figure FIG. 14. Development of a spatial wave from the surface of the resonator (lower graph) is provided by the side view. The graphs were made for heights z above the surface of the resonator, from z=0, lower graph, to z=0.02 mm for the last, upper graph. The wave attenuates after a height of 0.02 mm.

Figure 15:
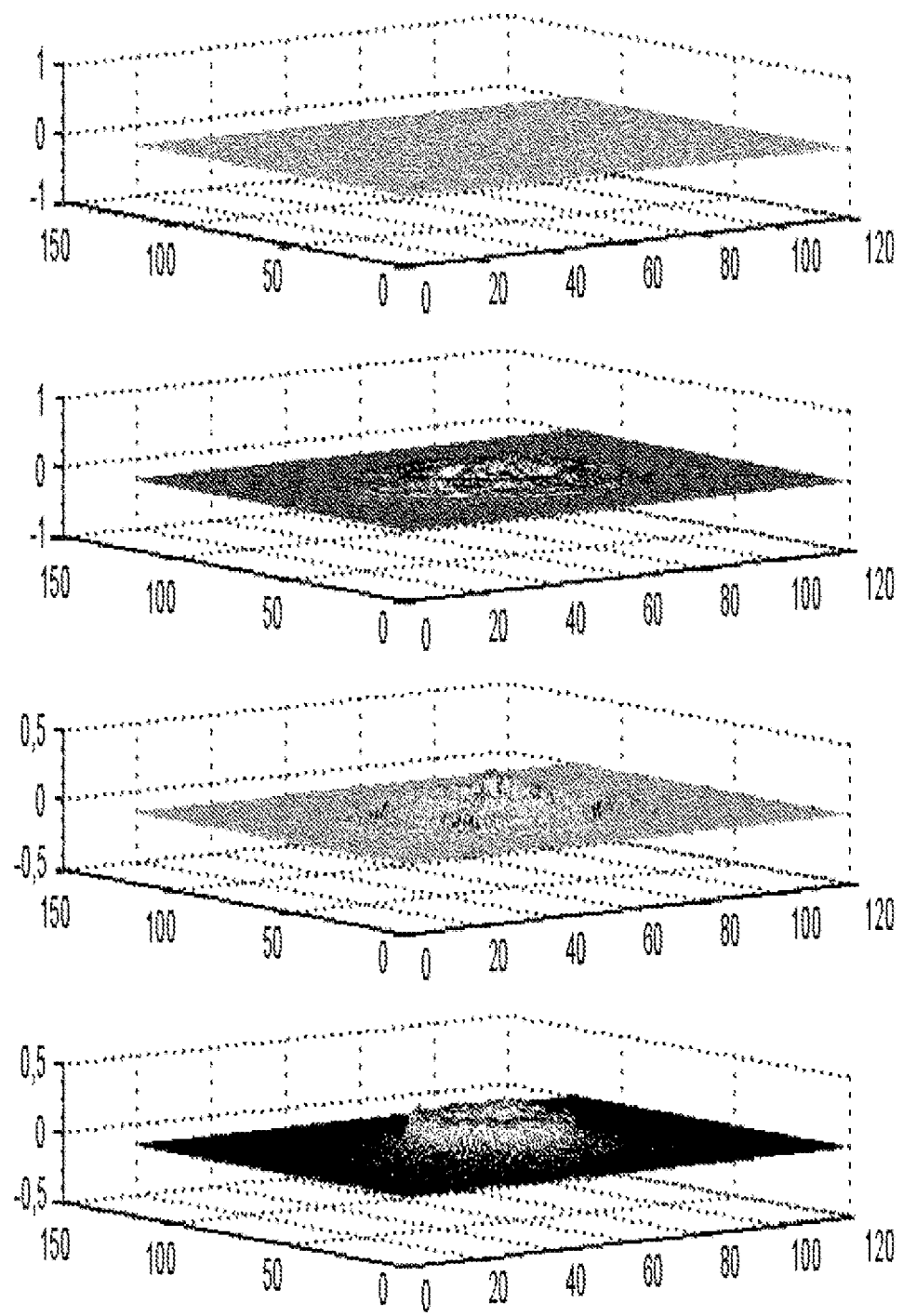
FIG. 15 is the strength distribution over height, to a height of 0.03 mm, with influence on 3 points with an ungrounded center.

The figure FIG. 15 also illustrates the strength distribution over height, to a height of 0.03 mm, with influence on 3 points with an ungrounded center.

Figure 16:
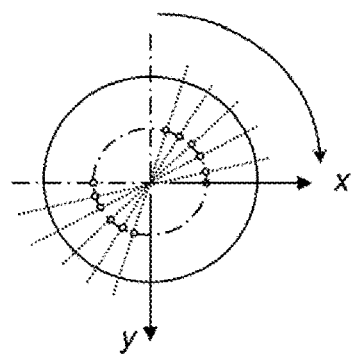
FIG. 16 is impulse effect on two opposite points with ungrounded resonator center.

Impulse effect on two opposite points with ungrounded resonator center. The field acts on diametrically opposite points on the surface of the resonator, which lie in the middle of the radii, a two-sided circuit (FIG. 16).

Figure 17:
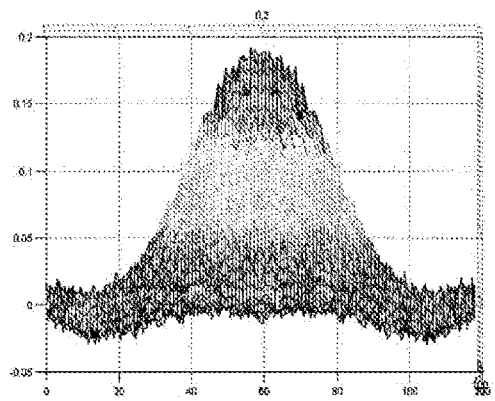
FIG. 17 is electric field strength above the resonator. Development of a spatial wave from the surface of the resonator (lower graph), side view.
Figure 17:
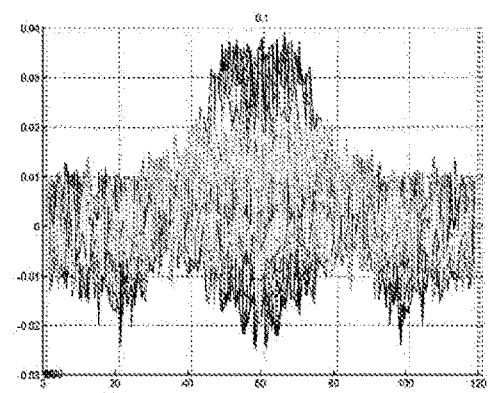
Figure 17:
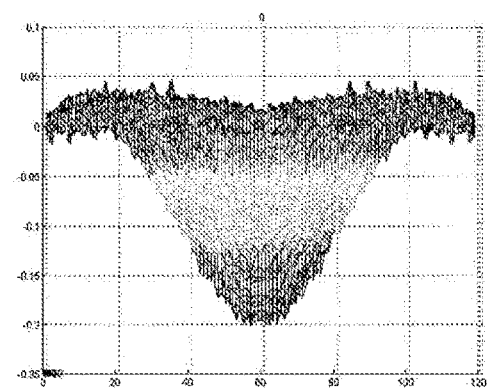

One of the modeling results is presented in FIG. 17 where electric field strength above the resonator is shown. This shows the development of a spatial wave from the surface of the resonator (lower graph), side view. The graphs of the distribution of the electric field strength in the figure were made for heights z above the surface of the resonator, from z=0, lower graph, to z=0.2 mm for the last, upper graph. The wave attenuates above a distance of 0.2 mm.

Figure 18:
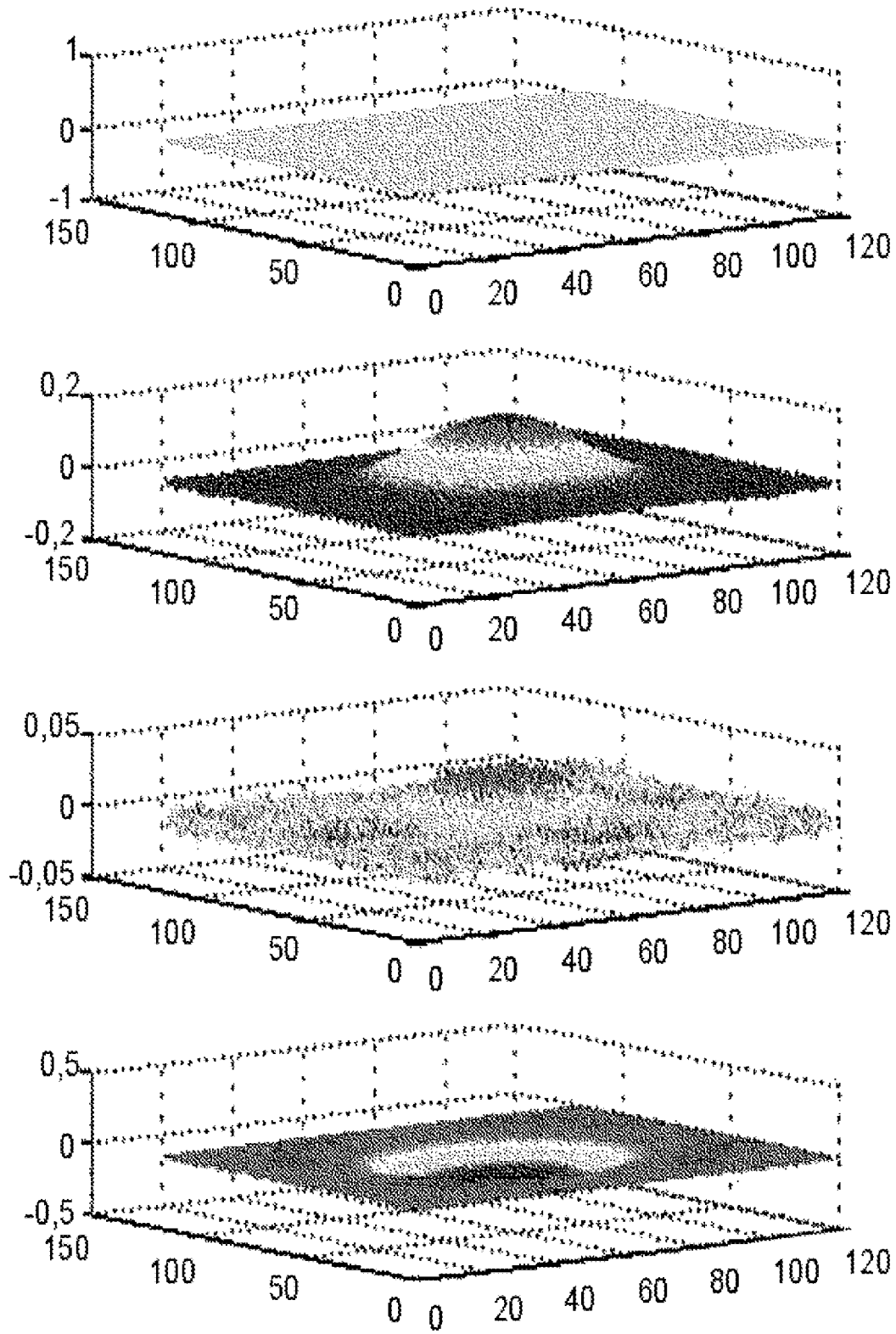
FIG. 18 is electric field strength on the surface of the resonator (lower graph, z=0) and so on in layers above the surface: 0.1 mm; 0.2 mm; 0.3 mm.

The figure FIG. 18 also illustrates the strength by height in the same sections from different positions. Electric field strength on the surface of the resonator (lower graph, z=0) and so on in layers above the surface: 0.1 mm; 0.2 mm; 0.3 mm. When z>0.2 mm, the wave decays.

Above the coordinate z=0.2 mm, the electric field strength becomes very small. The figure shows that it extends in breadth and the strength magnitude drops sharply with distance from the origin.

Figure 19:
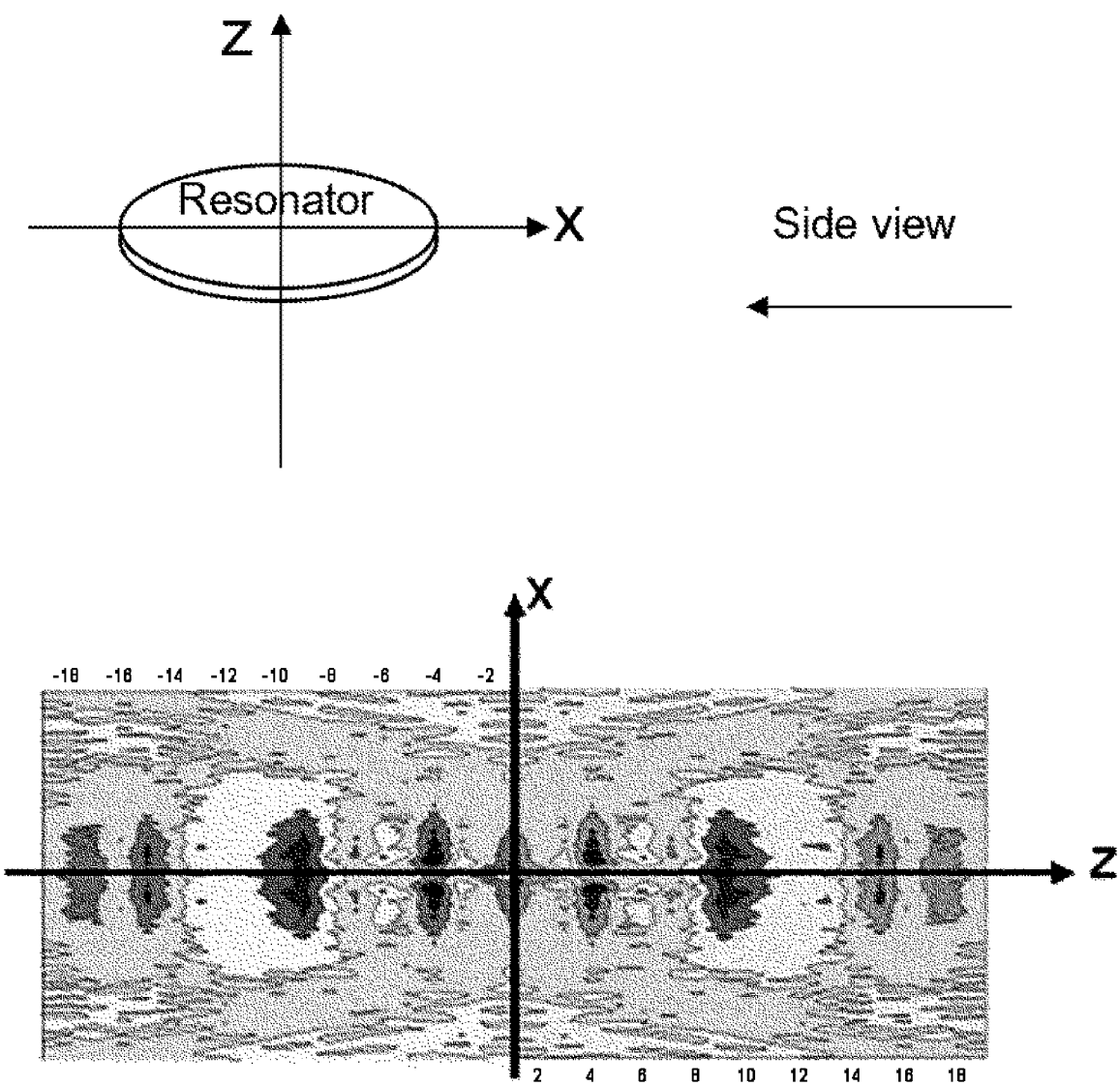
FIG. 19 is electric field strength for the steady state, when using a resonator with a double-sided design, side view.

Impulse effect on two opposite points with grounded resonator center and two-sided circuit. The development of an electric field during rotation and given influence on two opposite points on both sides of the resonator was investigated. The figure FIG. 19 presents the results of the calculation for the steady state, for a side view.

Figure 20:
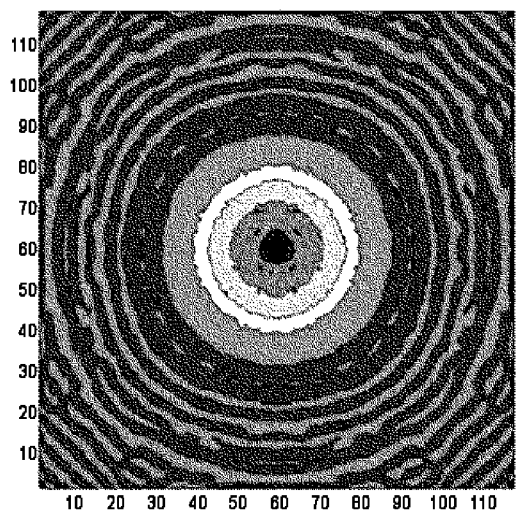
FIG. 20 is electric field strength: (a) on the resonator's surface; (b) at a distance of 0.1 mm above the surface of the resonator; (c) at a distance of 0.2 mm; (d) at a distance of 0.3 mm; (e) at a distance of 0.4 mm; (f) at a distance of 0.5 mm; (g) at a distance of 0.6 mm; (h) at a distance of 0.7 mm; (i) at a distance of 0.8 mm; (k) at a distance of 0.9 mm; (l) at a distance of 1 mm; (m) at a distance of 1.1 mm; (n) of at a distance 1.2 mm; (o) at a distance of 1.3 mm; (p) at a distance of 1.4 mm; (r) at a distance of 1.5 mm; (s) at a distance of 1.6 mm; (t) at a distance of 1.7 mm.
Figure 20:
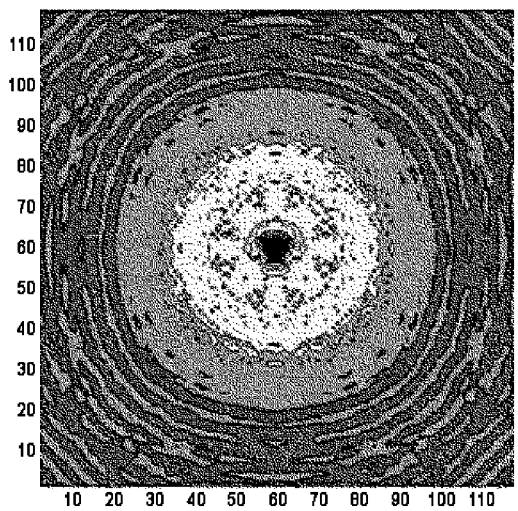
Figure 20:
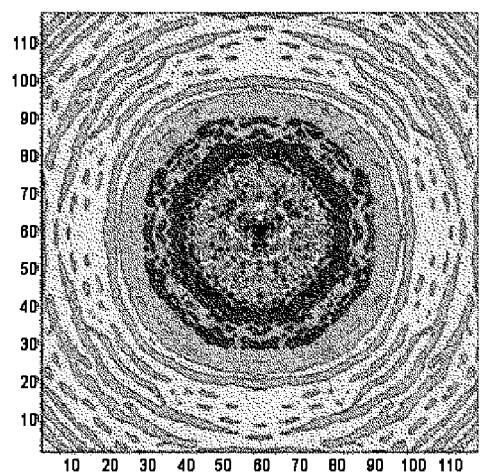
Figure 20:
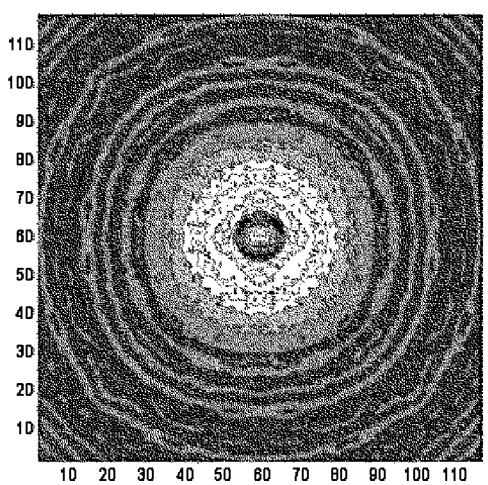
Figure 20:
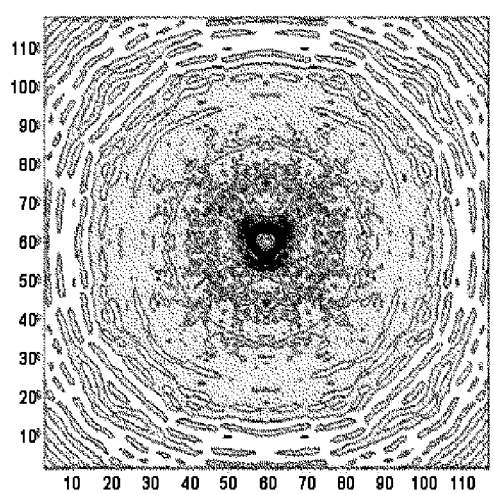
Figure 20:
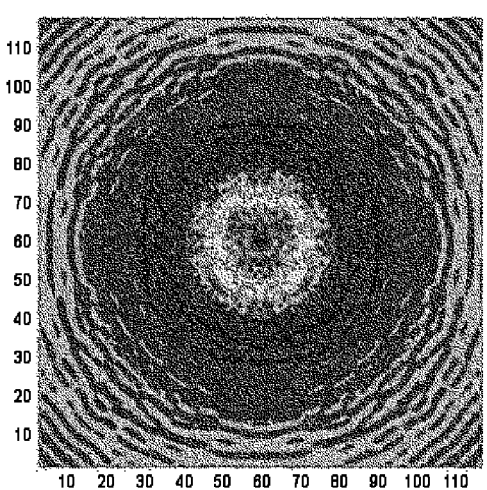
Figure 20:
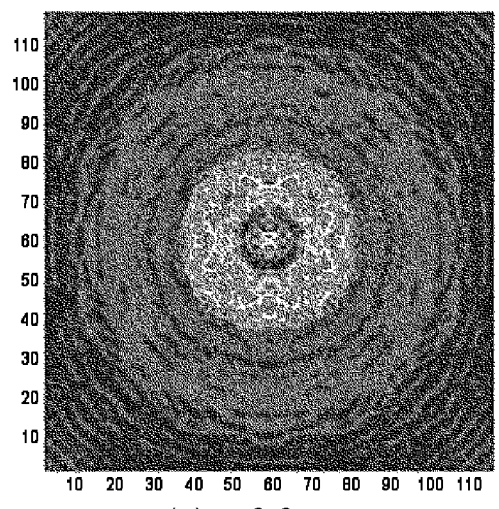
Figure 20:
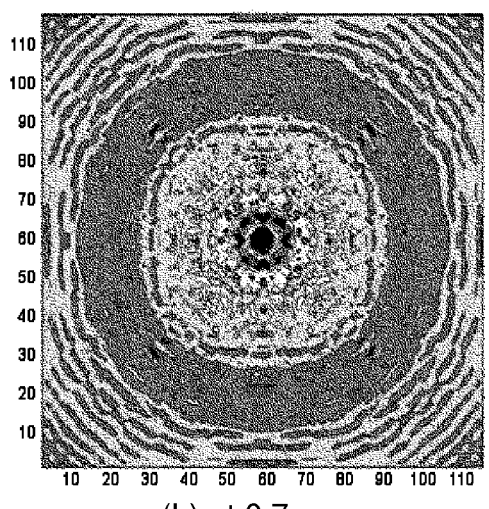
Figure 20:
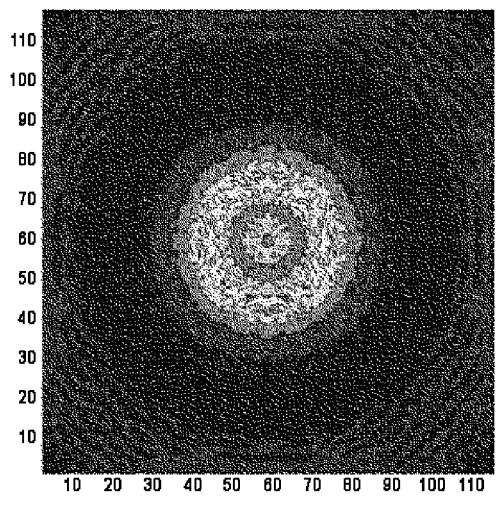
Figure 20:
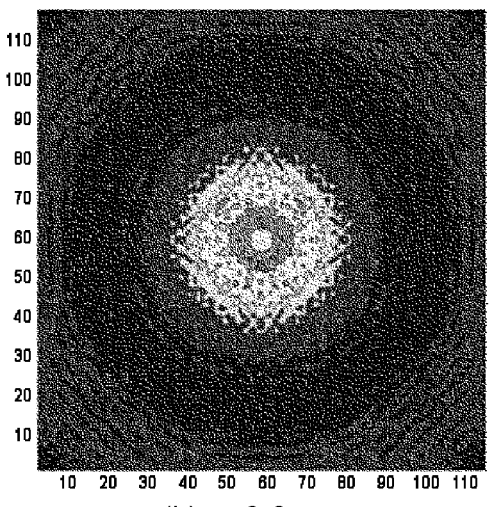
Figure 20:
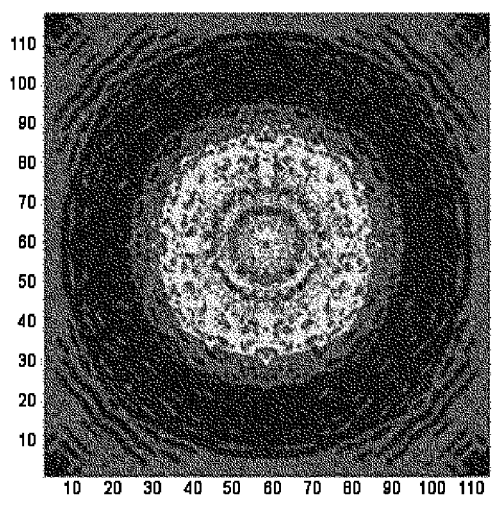
Figure 20:
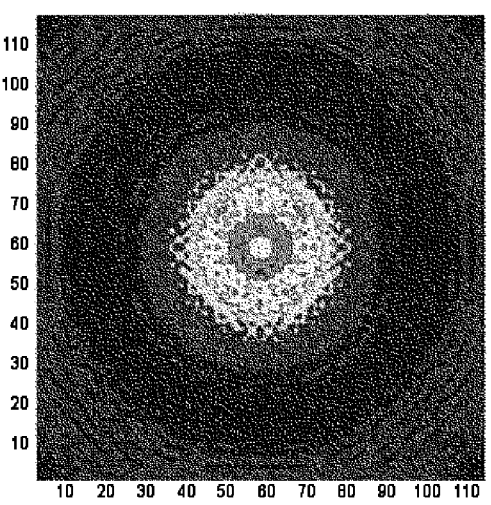
Figure 20:
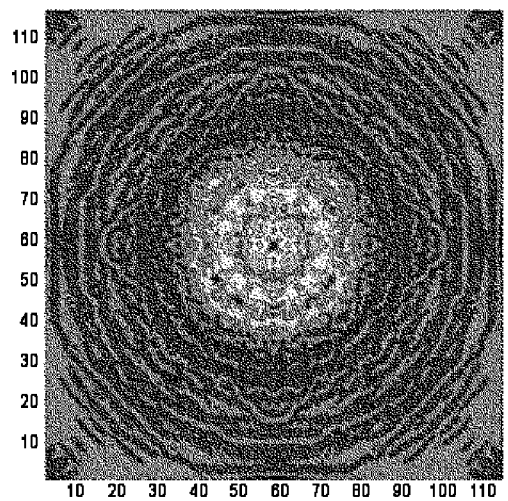
Figure 20:
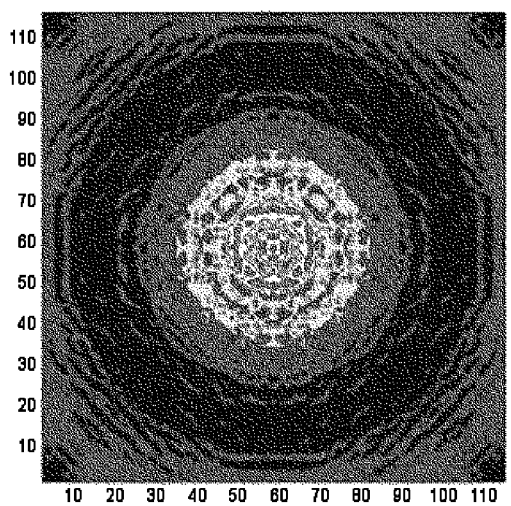
Figure 20:
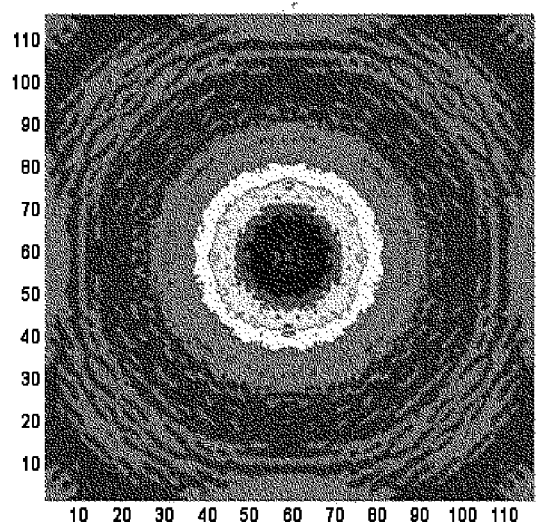
Figure 20:
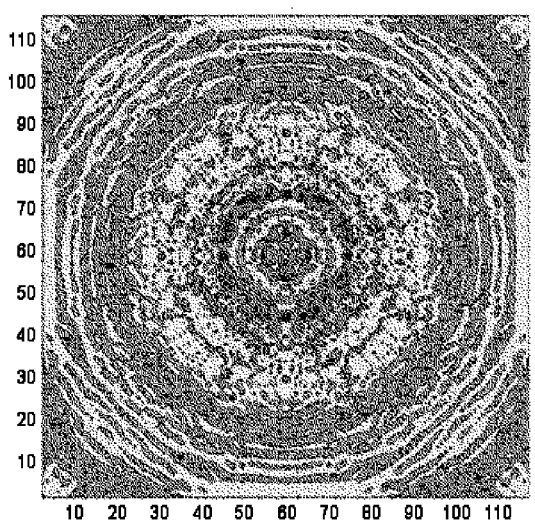
Figure 20:
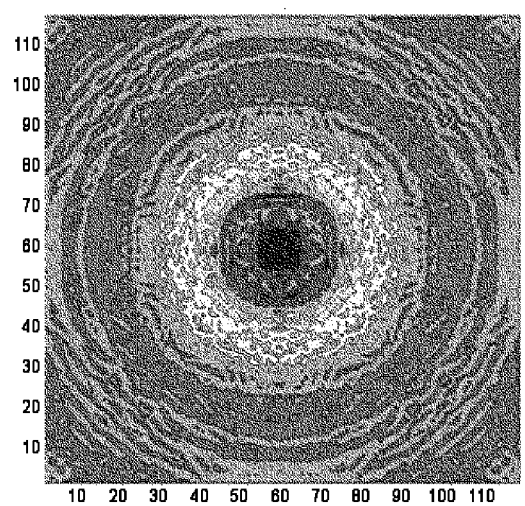
Figure 20:
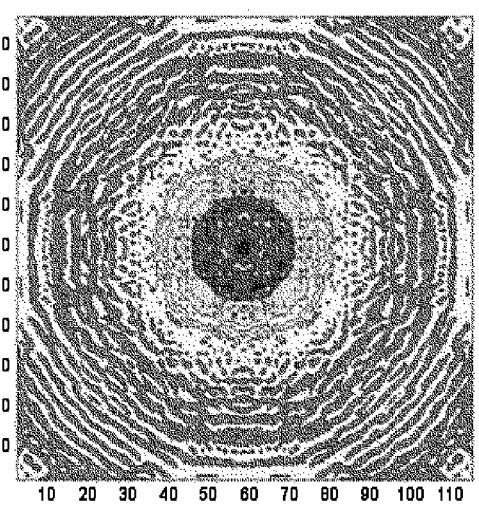

The figures FIG. 20 from FIG. 20a to FIG. 20t present the same result layer by layer for heights from 0 mm to 1.7 mm above the resonator's surface.

Figure 21:
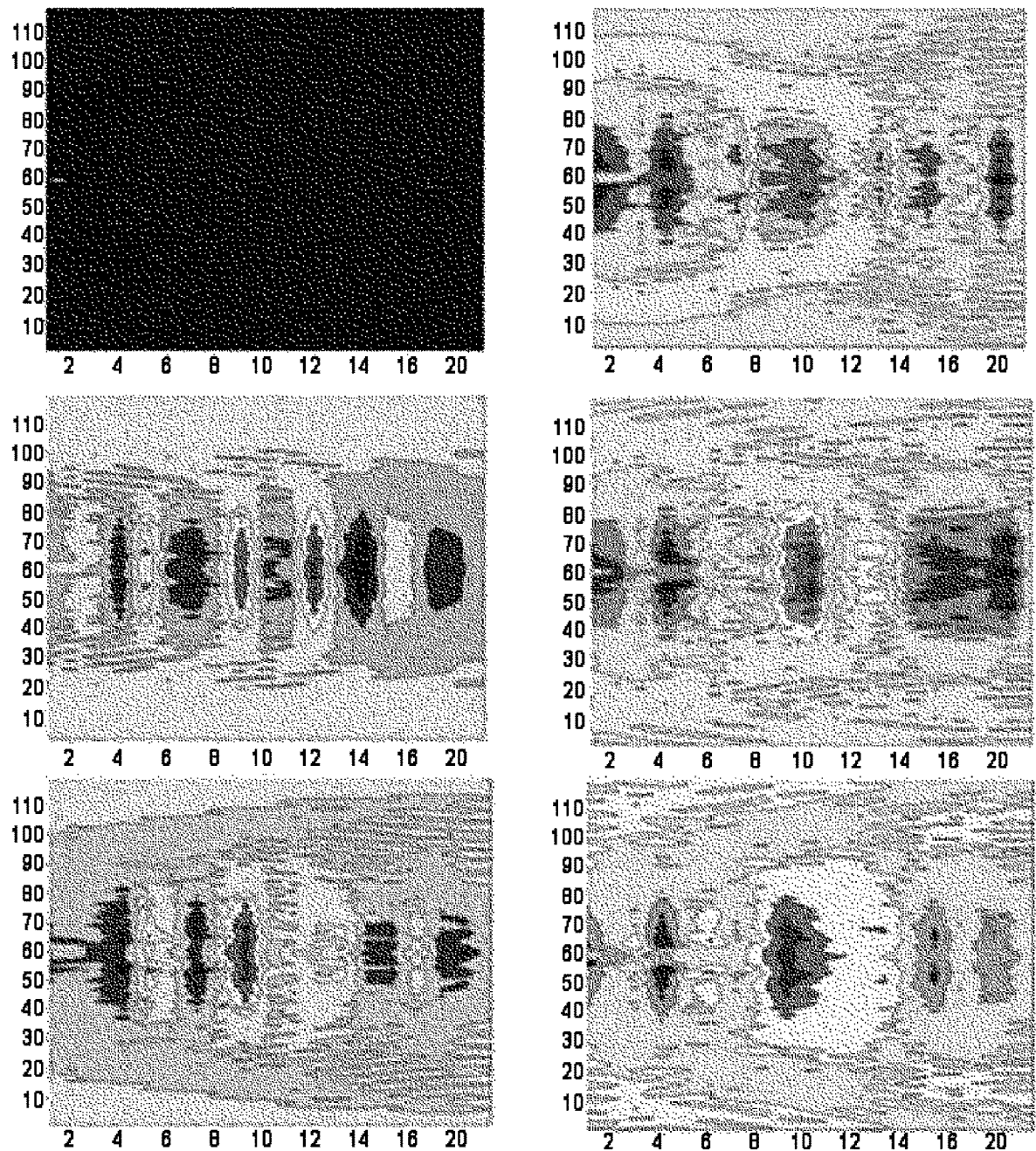
FIG. 21 presents dynamics of changes in the strength of the field above the wafer.

The figure FIG. 21 presents the results of modeling using a three-dimensional non-stationary model (6), i.e., dynamics of changes in the strength of the field above the waffer. The upper left figure is time moment 1. The middle left figure is time moment 2. The lower left figure is time moment 3. The upper right figure is time moment 4. The middle right figure is time moment 5, and the lower right figure is time moment 6.

Figure 22:
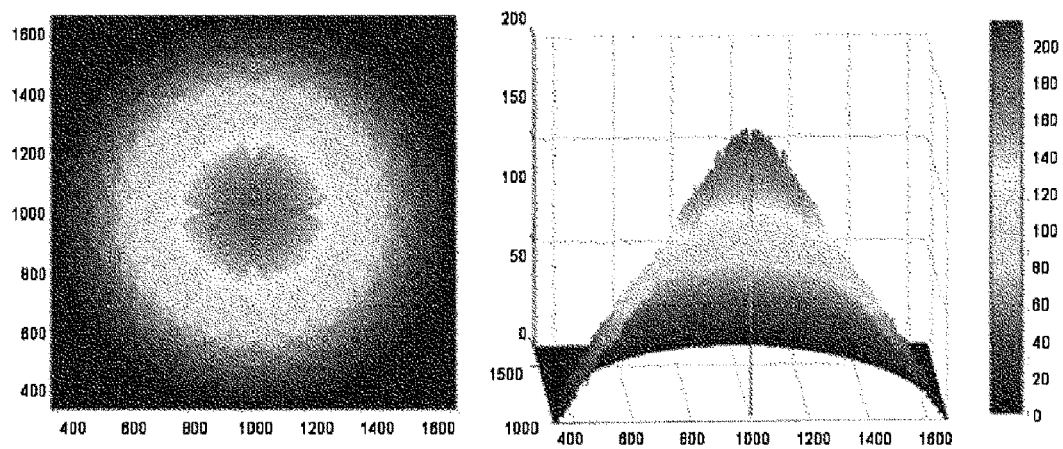
FIG. 22 presents distribution of field strength E above the resonator from 0.28 to 14.18 (V/m) with incident radiation at 2.4 GHz.
Figure 23:
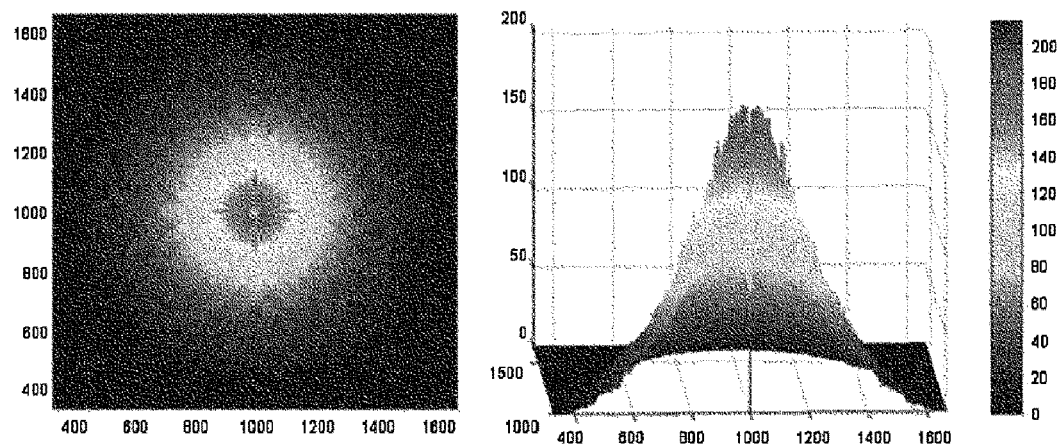
FIG. 23 presents distribution of field intensity I above the resonator from 0.08 to 201.05 (W/m$^2$) with incident radiation at 2.4 GHz.

The change in the development of the wave along the z-axis, which is orthogonal to the wafer's surface, can be seen clearly in the figures FIG. 22 and FIG. 23. The wafer is located on the left and occupies the position whose borders are denoted in the middle left figure by two bars. Given a wafer with a diameter of 6 mm, the wavelength along the z-axis is approximately 1.1 mm. The radiation incident upon the wafer was white noise. FIG. 22 shows distribution of field strength E above the resonator from 0.28 to 14.18 (V/m) with incident radiation at 2.4 GHz. FIG. 23 shows distribution of field intensity I over the resonator from 0.08 to 201.05 (W/m$^2$) with incident radiation at 2.4 GHz.

Thus, the self-affine surface topography transforms the radiation incident on it into a coherent form, even for a wide range of frequencies.

It was shown in [1] that a coherent transformer, when excited by EM radiation, forms a stationary, multi-frequency coherent wave (hologram) in space, which is stable and soliton-like regardless of the boundary conditions [2]. Its shape does not change with changing boundary conditions. This means that the result of this transformation does not depend on the characteristics of the radiation incident on it.

Our experiments have demonstrated that a semiconducting wafer with a self-affine topology on its surface transforms a broad spectrum of incident radiation into a coherent form. It redistributes the incident radiation in terms of its wavelength as well as its phase, in accordance with its topography. Its use opens up fundamentally new opportunities for creating a variety of devices:

coherent transformers that harmonize the interaction of several wave fronts;

broadband resonators with distribution of energy through a space that is self-similar and carries information about the amplitude, wavelength, and phase of incident radiation.

This development will find application in the form of a protective device that transforms external radiation, including 5G communication systems (3.5-28 GHz), into a form that is harmonized with the inherent radiation of an organism's cells, thus making it safe for a biological object.

Based on the fact that biological objects are open physical systems that have an EM nature and function under conditions of constant exchange of energy and matter with the environment, they have a specific design for fixing the set of the molecular structural lattice's nodal centers, which are interconnected in a unified spatial matrix. Since the molecular structural lattice reflects a specific model of the fundamental interrelationships of the object, it is possible to consider the biological organization as an organization that initiates a constant EM superposition. This superposition is able to react by means of its own resonance to any particular external impulse, causing changes in the molecular structure that gave rise to it, making it possible to have a targeted effect on the biological object.

As a result of the counter-harmonization of technogenic radiation interacting with the BO's own electromagnetic radiation, which is a superposition of cellular metabolism processes, the coherent transformer used in this method initiates optimization of the organism's adaptive physiological characteristics, thereby making the interaction conflict-free, which is proven by experimental data.

The essence of the claimed method is as follows.

The method for protecting biological objects from the negative influence of technogenic EM radiation in a wide range of frequencies, which includes creating around a biological object (BO) or between it and the source of technogenic EM radiation a special EM field in the form of a fractal coherent matrix (hologram), using a fractal-matrix coherent transformer to create the field.

The coherent transformer used is a self-affine lattice (resonator), formed from circular topological lines, creating a slit-like raster.

The resonator's structural lattice is a Fourier transformer that harmonizes the amplitudes, phases, frequencies and polarization vectors of external technogenic radiation and the BO's inherent EM radiation. The coherent field that forms around the resonator resonates with the surrounding EM waves, including with the inherent radiation of the human body's biological cells, transforming it into a consistent form, and makes the interaction conflict-free.

The resonator's coherently transforming impulse forms a spatial matrix whose multilevel gradation is a set of annular raster lattices symmetric with at least the three orthogonal basis vectors X, Y, Z with a subsequent release to multidimensionality N and with the formation of a spatial monostructural form with an infinite number of inherent components satisfying Noether's theorem, which requires the formation of the maximum spatial symmetry of the object's field structure, and the condition of interaction in the form of a self-affine hypersphere.

$$\sum_{k=1}^{n} X^k + \sum_{k=1}^{n} Y^k + \sum_{k=1}^{n} Z^k + \ldots + \sum_{k=1}^{n} N^k \to 0,$$

where X, Y, Z, N are the fractalization vectors of the system of a annular self-affine circuit, k=1 ... n is the number of circuit elements.

According to the Noether theorem, each continuous symmetry of a physical system corresponds to a certain law of conservation. In our case, the symmetry of the diffraction grating, formed from annular topological lines, unambiguously forms a coherent EM field, which is a hologram as a stable wave structure. This is confirmed by the principle of holograms (D. Gabor-Yu. N. Denisyuk), according to which any wave superposition carries the same properties as the regular structure that generated it.

During the proposed exposure to a coherently transformed EM field, the complex of the wave characteristics of the inherent radiation of the cells of a biological object is brought into a resonant state that is determined by strict fractal-matrix schematization, which causes the system to respond. Such counter-harmonization of the wave characteristics, by eliminating conflict, leads to the stabilization of all metabolic processes and, as a result, an increase in the BO's adaptive abilities under conditions of exposure to technogenic EM radiation [3, 4].

The wave characteristics and stabilization of the metabolic processes of the BO are harmonized by exposing it to an EM field coherently transformed by the resonator's self-affine annular grating. For the resonator's self-affine annular grating, we used the fractal-planar projection of a special spatial structural-holographic construction, fixed on a solid medium and formed from annular topological slit-like lines that create a raster (RF Patent No. 2231137, No. 2217181, No. 2284062).

Figure 24:
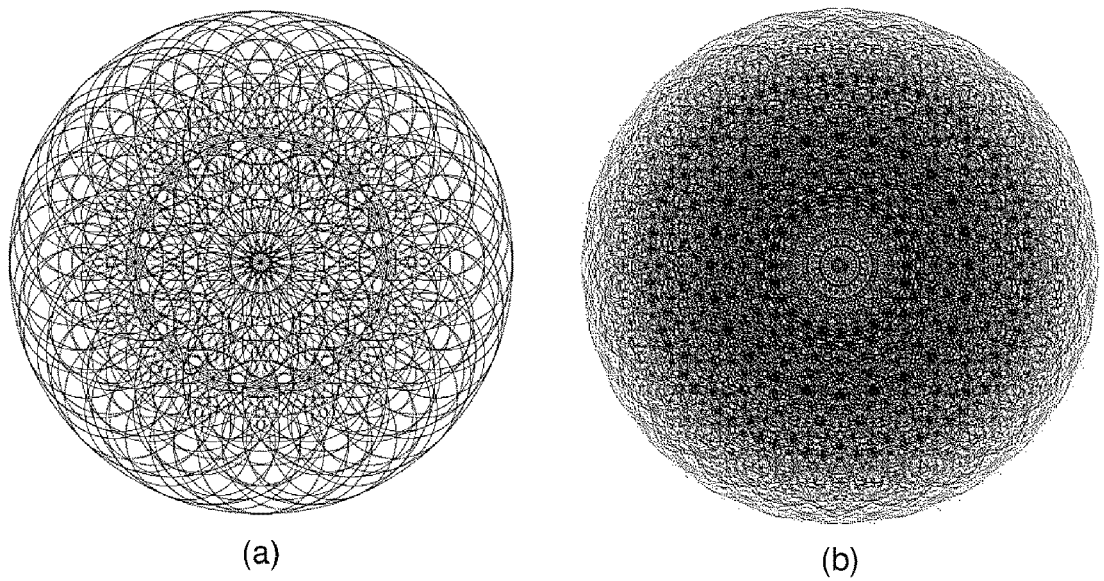
FIG. 24 presents simplified versions of planar projections of the spatial structural-holographic self-affine matrix of the resonator's coherently transforming field response.

The figures FIG. 24a and FIG. 24b show simplified versions of planar projections of the spatial structural-holographic self-affine matrix of the resonator's coherently transforming field response.

The coherently transforming resonator can be made in various embodiments, depending on its location, and be directly on the BO (attached to clothing, hung from a cord, etc.), near the biological object BO (for example, in the same room), attached to the source of technogenic EM radiation (mobile phone, computer, home appliances, etc.) or be between the BO and the radiation source.

The proposed method for protecting biological objects from technogenic EM radiation contributes to a reduction (elimination) of the negative influence of technogenic EM radiation on the BO, especially with the spread of 5G communication systems. This method makes it possible to protect a biological object from the negative influence of broadband EM radiation.

The claimed method has no analogues and can be used in the daily life of a person that exists among a large number of electronic devices emitting an EM field.

CITATION LIST

Patent Literature

Patent application WO1997034459A2, patent RU2194376. L. Eriksson. Method of producing a metallic layer on the surface of a detail for shielding against electromagnetic radiation.

■Patent RU2265898C2. Voronin I. V. et al. Method for manufacturing a screen for protection from electromagnetic emission.

Patent application DE10039125A1/Patent RU2234175C2. J. T. Kuehnert et al. Electromagnetic absorbing material and method for manufacturing this material and shielding devices.

Non Patent Literature

1. Kopyltsov A. V., Serov I. N., Lukyanov G. N. Interaction of a Semiconducting Wafer with a Self-Affine Surface Topography with Electromagnetic Radiation. Nanotechnology.—2006.—No. 4(8).—pp. 44-49.
2. Serov I. N., Lukyanov G. N., Kopyltsov A. V. Mathematical Modeling of the Interaction of Electromagnetic Radiation with a Silicon Self-Affine Surface. ENGECON Bulletin, "Technical Sciences" series—2007 Issue 6(19)—pp. 199-205.
3. Serov I. N., Sysoyev V. N., Rybina L. A., Ananeva V. N., Effect of products with a nano-scale fractal topology on several vital processes and human ecology, Nanotechnology, 2006, April, No. 1, pp. 146-151.
4. Serov I. N., V. N. Sysoyev., Evaluation of the effectiveness of using Aires Shield electromagnetic anomaly neutralizers to reduce the negative influence of the electromagnetic field caused by the operation of a cellular phone, International Journal of Applied and Fundamental Research.— 2014.— No. 8—pp. 81-85.
5. Slabko V. V., Principles of Holography, Soros Educational Journal, No. 7, 1997.
6. D. Gabor."*Holography* (1948-1971)". *Nobel Lecture, Advances in the Physical Sciences*, Vol. 109, Issue 1, January 1973.
7. Yu. N. Denisyuk. Principles of Holography.— Leningrad: Publishing House of the State Optical Institute, 1979.

8. A. S. Mitrofanov. Principles of amplification of optical radiation. Teaching aid. Saint Petersburg. Saint Petersburg State University of Information Technologies, Mechanics, and Optics, 2005.
9. Potapov A. A., Fractals in Radiophysics and Radiolocation: Topology of the Sample. Edition 2, revised and added to.— Moscow: Universitetskaya Kniga, 2005.
10. Mandelbrot, V. V., *Self-affine fractals and fractal dimension*, Physica Scripta 32 (1985) 257-260.
11. Nguyen V D, Bouisset P, Kerlau G, Parmentier N, Akatov Y A, Archangelsky V V, Smirenniy L N, Siegrist M. A new experimental approach in real time determination of the total quality factor in the stratosphere. Rad. Prot. Dos. 1993; 48(1): 41-46.
12. Johansen Ch. Electromagnetic fields and health effects— epidemiologic studies of cancer, diseases of the central nervous system and arrhythmia-related heart disease. *Scand J Work Environ Health* 2004; 30 Suppl 1: 1-80.
13. Hardell L, Sage C. Biological effects from electromagnetic field exposure and public exposure standards. *Biomedicine & Pharmacotherapy* 2008; 62: 104-109.
14. Terzia M, Ozberka B, Denizb O G, Kaplanb K. The role of electromagnetic fields in neurological disorders. *J. Chem. Neuroanatomy.* 2016; 75: 77-84.
15. Repacholi M H, Basten A, Gebski V, Noonan D, Finnie J, Harris, AW. Lymphomas in E mu-Pim1 transgenic mice exposed to pulsed 900 MHz electromagnetic fields. *Radiation Research.* 1997; 147(5): 631-640.
16. Phillips J L, Singh N P, Lai H. Electromagnetic fields and DNA damage. *Pathophysiology* 2009; 16(2-3): 79-88.

The invention claimed is:

1. The method for protecting a biological object from the negative influence of technogenic electromagnetic radiation in a wide range of frequencies, characterized in that it includes creating around the biological object or between the biological object and the source of technogenic electromagnetic radiation a special electromagnetic field in the form of a fractal coherent matrix.

2. The protection method according to claim 1, characterized in that the field is created using a fractal-matrix coherent transformer which is a self-affine lattice of annular topological lines creating a slit-like raster.

3. The protection method according to claim 1, characterized in that the coherent transformer forms an electromagnetic field in the form of a spatial holographic matrix.

4. The protection method according to claim 1, characterized in that the transformer's electromagnetic field transforms the technogenic electromagnetic radiation into the form of a spatial coherent matrix of harmonized electromagnetic wave superpositions.

5. The protection method according to claim 1, characterized in that depending on the nature of the negative influence, different options for placement of the coherent transformer are used: on a biological object.

6. The protection method according to claim 1, characterized in that depending on the nature of the negative influence, different options for placement of the coherent transformer are used: on a source of technogenic electromagnetic radiation.

7. The protection method according to claim 1, characterized in that depending on the nature of the negative influence, different options for placement of the coherent transformer are used: between a biological object and a source of technogenic electromagnetic radiation.

* * * * *